United States Patent [19]

Kallabis et al.

[11] Patent Number: 4,840,633
[45] Date of Patent: Jun. 20, 1989

[54] CEMENTLESS ENDOPROSTHESIS

[76] Inventors: Manfred Kallabis, Falkenweg 24;
Guido Gombert, Schillerstr. 18, both of D-8960 Kempton, Fed. Rep. of Germany

[21] Appl. No.: 137,257

[22] Filed: Dec. 23, 1987

[30] Foreign Application Priority Data

Jan. 3, 1987 [DE] Fed. Rep. of Germany ....... 3700102
Jul. 31, 1987 [DE] Fed. Rep. of Germany ....... 3725387

[51] Int. Cl.⁴ .................. A61F 2/32; A61F 2/30
[52] U.S. Cl. ................................. 623/23; 623/18
[58] Field of Search ............... 623/16, 18, 19, 20, 623/21, 22, 23; 128/924 Z, 924 F, 924 Y

[56] References Cited

U.S. PATENT DOCUMENTS

| | | | |
|---|---|---|---|
| 4,259,072 | 3/1981 | Hirabayashi et al. | 623/23 |
| 4,407,022 | 10/1983 | Heimke et al. | 623/23 |
| 4,645,506 | 2/1987 | Link | 623/23 |
| 4,681,590 | 7/1987 | Tansey | 62/23 |

FOREIGN PATENT DOCUMENTS

| | | | |
|---|---|---|---|
| 0190981 | 8/1986 | European Pat. Off. | 623/22 |
| 2558446 | 7/1976 | Fed. Rep. of Germany | 623/23 |
| 1012903 | 4/1983 | U.S.S.R. | 623/23 |

*Primary Examiner*—Richard J. Apley
*Assistant Examiner*—David J. Isabella
*Attorney, Agent, or Firm*—Notaro & Michalos

[57] ABSTRACT

An endoprosthesis (10) is composed of a stem (12) tapering to the distal end thereof and a screw spindle (38) having a broadflanged helical flank (42). The stem is provided with a helical slot (36) guiding flank (42) of spindle (38) during assembling of the prosthesis. The flank (42) projects outwards from both broad side faces (14) of the stem and forms a plurality of broad flanged thin supporting ribs in the proximal portion of the prosthesis (10), the ribs cutting not only into the cancellous bone structure but also into the cortex. The prosthesis (10) provides for a load transmission exclusively into the proximal femur portion, while the distal portion is free of axial loads.

12 Claims, 1 Drawing Sheet

CEMENTLESS ENDOPROSTHESIS

BACKGROUND OF THE INVENTION

The invention relates to a cementless endoprosthesis primarily for hip joints comprising a screw spindle to be screwed into the medullary bone canal, a conical neck mechanically connected with the proximal end of the screw spindle, the axis of the neck angularly arranged with respect to the axis of the screw spindle.

An endoprosthesis of this kind has been published 1948 by McBride. Because the core of the screw spindle must transmit extreme forces the diamter must be as great as possible. McBride has proposed to drill a bore into the medullary bone canal to cut a thread and to screw in the screw spindle containing the neck for a head of the prosthesis. The thread of the spindle should be anchored in the cancellous bone structure to provide a fixation of the spindle. However, it has been recognized, that this art of arthroplasty has a plurality of deficiencies. The medullary bone canal is not straight but antecurved. The bone is necessarily weakened in some areas by drilling the straight bore. Just in these weakened areas of the bone the best anchoring effect of the spindle is gained. Because of the curvature of the bone canal there remain broad surfaces of the canal with which the thread of the spindle does not come into engagement. Because the proximal femur portion opens in a bell-shaped manner, the spindle stands free in this area. The thread cuts into the cortex at the distal end of the spindle and because the cortex structure is much stronger than the cancellous structure the prosthesis is supported substantially at its distal end. The result is a permanent proximal relief and weakening of the proximal load suspension structures and the biomechanical response is an atrophy of the bone structures which increases from proximal to distal. Further deficiencies consist in that the height of the thread flank could only be small in order not to weaken the core of the spindle so that the thread provides only a small form-fit engagement and last but not least in that the spindle cannot be firmly held against rotation.

Another type of endoprosthesis known as "Spotorno Prosthesis" which is used nowadays consists of a stem tapering to its distal end and having oblong cross-sections somewhat adapted to the shape of the medullary canal of the bone. The stem is beaten axially into the canal and wedges itself therein. A plurality of longitudinal ribs are provided at the broad side faces of the proximal portion of the stem to prevent any rotation of the stem. However, also this kind of endoprosthesis is not satisfactory because press-fit anchoring takes place only at its distal end in the cortex of the bone canal and the results are the same as mentioned above.

SUMMARY OF THE INVENTION

One object of the invention is to provide a cementless endoprosthesis which allows load transmission into the proximal femur portion.

A further object of the invention is to provide a cementless endoprosthesis which can be anchored in the proximal cancellous bone structure avoiding any wedging at the distal end thereof.

A further object of the invention is to provide a cementless prosthesis for axial insertion into the medullary bone canal, which is provided with broad cross-wise supporting ribs projecting into the proximal cancellous bone structure and which nevertheless do not injure or damage the cancellous structure during axial insertion.

A further object of the invention is to provide an endoprosthesis comprising a multipart arrangement, in which one part is adapted to fit non-rotatably in the bone canal and a second part to be guided by and fastened in said inserted one part, whereby the second part carries lateral supporting ribs which enter or cut into the cancellous structure of the proximal femur.

One further object of the invention is to provide a novel prosthesis comprising an axially insertable stem having an integral neck for fastening a head, and a helical member threadably guided by the stem.

A further object of the invention is to provide an endoprosthesis comprising a stem, a helical slot within the stem, and screw spindle in thread-engagement with the slot of the stem, whereby the helical slot is open at opposite broad faces of the stem and a broad-flanged helical web or flank of the spindle engages with the slot and projects outwards from both broad faces of the stem, while the core of the spindle is arranged within the contours of the stem.

According to the invention the stem is inserted into the medullary bone canal without any beating. The distal end of the stem hangs free in the canal. Then the screw spindle is screwed into the stem, which serves as a guiding and supporting frame for the spindle.

According to one embodiment of the invention the helical flank of the spindle is of frusto-conical contour, so that the preferably self-cutting flank increasingly cuts deeper into the cancellous bone structure of the proximal femur portion. Thanks to the inventive concept the stem forms reinforcement and stiffening means for the spindle which therefore needs only a core of a small diameter whereas the helical flank of the spindle is designed to have an outside diameter at the proximal end which is at least 3 times as great as the core diameter. Therefore, the lateral ribs resulting from the broad-flanged flank of the spindle cut deeply into the cancellous bone structure and even into the surrounding cortex of the proximal femur portion. Any bone substance loss is avoided, because the medullary canal need not be drilled.

It should be understood, that the spindle extends only in the proximal half of the stem if this is of usual length. The distal portion of the stem, by no means has any axial supporting effect. Therefore, it is possible to shorten the stem distally.

According to a further embodiment of the invention the stem is provided with at least one window which is longitudinally passed by the spindle. Cavities are formed between the spindle core and stem legs at opposite sides of the window so that cancellous bone material can ingrow into and through the cavities to increase the anchoring effect of the prosthesis.

Further features and advantages of the invention will become apparent from the following detailed description of a preferred embodiment of the invention and the claims.

DESCRIPTION OF A PREFERRED EMBODIMENT

Figure 1:
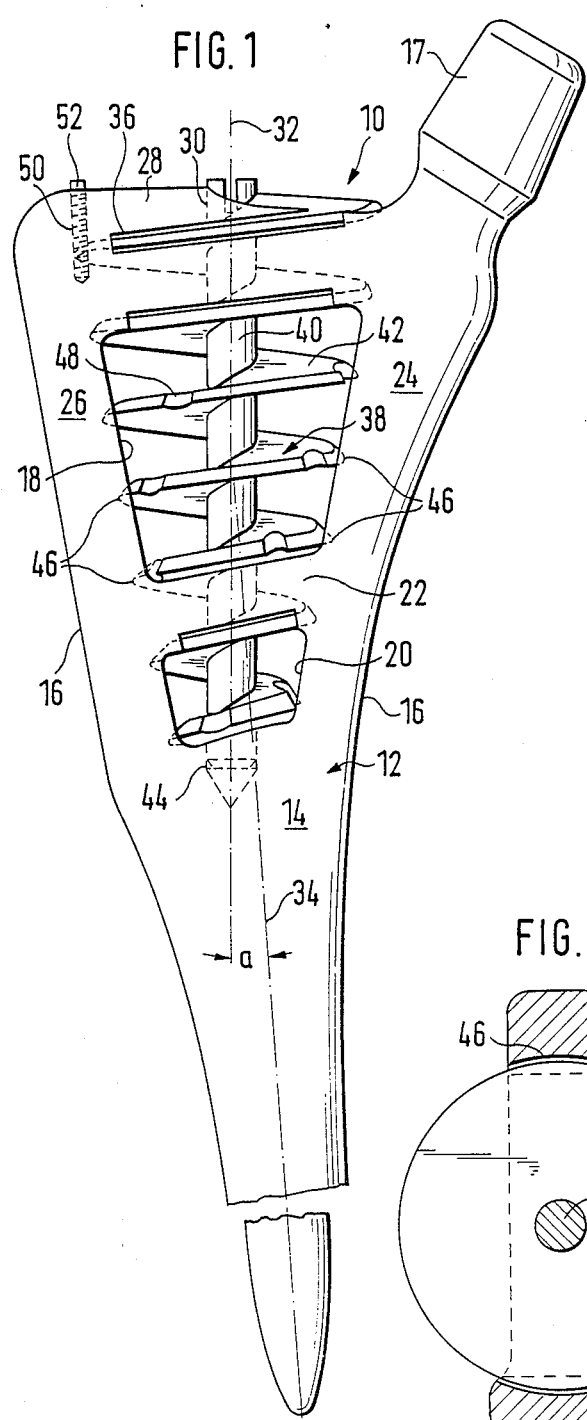
FIG. 1 shows a side view of a prosthesis.
Figure 2:
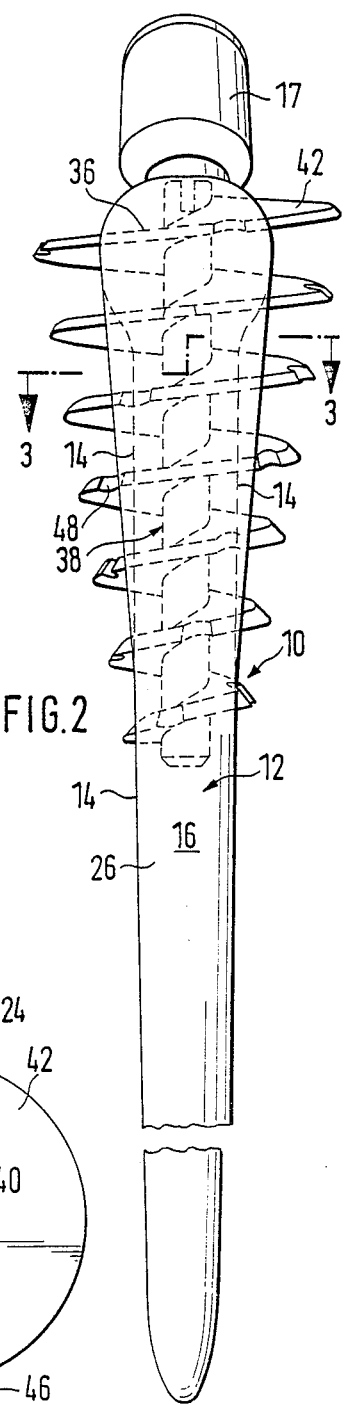
FIG. 2 shows an end view of the prosthesis as seen in direction to the neck thereof.
Figure 3:
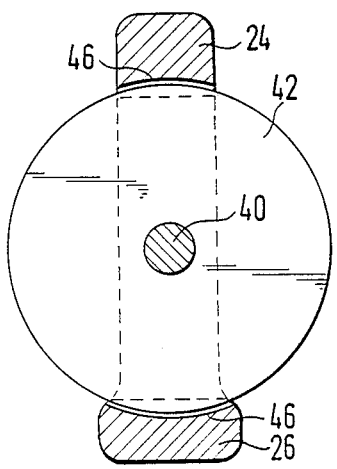
FIG. 3 shows a cross-sectional view taken along line 3—3 of FIG. 2.

An endoprosthesis 10 comprises a stem 12 of a titanium alloy the broad side faces 14 thereof tapering from the proximal end to the distal end. The thickness of the stem measured at small end faces 16 of the stem 12 reduces slightly to the distal end. At the upper right end (FIG. 1) of the stem 12 a conical neck 17 is integrally associated, which serves for fastening a head as it is usual practice.

Two windows 18,20 are provided in the proximal area of the stem 12. The windows 18, 20 extend completely through the stem in rectangular direction to the side faces 14. A web 22 remaining between the windows 18,20 serves for increased stability. A pair of proximally diverging legs 24,26 are formed between the end faces 16 and the windows 18,20 respectively. The legs 24,26 are integrally connected with one another by a bridge 28, which is slightly torically thickened with respect to the side faces 14. That leg 26 which is opposed from neck 17 is enlarged at both side faces to adapt the cross-section of the stem 12 to that of the medullary bone canal.

A bore 30 passes through the bridge 28 along an axis 32 which forms an angle a of about 5 degrees with the longitudinal axis 34 of the stem 12. With respect to the axis of neck 17 the axis 32 forms a smaller angle than axis 34. Thereby the windows 18, 20 are centrally positioned in the stem. The web 22 is provided with a bore coaxial with bore 30 and of the same diameter. A helial slot 36 is provided in the bridge 28. The slot 36 communicates with bore 30 and runs coaxially therewith. The slot 36 opens at the upside and bottom faces of the bridge 28 and at both broad side faces thereof. Thanks to the helial form of the slot 36 the legs 24,26 remain integrally connected in the region of the bridge 28 by bridge portions which run above the slot 36 in one axial half of stem 12 and below the helical slot 36 in the other axial half. The bore in the web 22 communicates also with a helical slot substantially equal with slot 36.

Both legs 24,26 are provided with grooves 46 cut into the inner surfaces facing one another. The slot 36, the grooves 46 which are segment- or ring-shaped and the slot in the web 22 are precisely arranged on one and the same helical path the outside contour of which runs along an imaginary truncated cone.

A screw spindle 38 is screwed into the stem 12 along the axis 32. The screw spindle 38 is composed of a cylindrical core 40 of circular cross-section and a broad-flanged thread in the form of a helical flank or rib 42 which tapers conically to the distal end. The coning angle amounts to 20°. The thickness of flank 42 reduces slightly from a constant foot width of about 2 mm radially outwards and it should be clear that the lead of the flank is absolutely constant and amounts to 11°. The dimensions of the slot 36 in the bridge 28 and in the web 22, i.e. height of the slot and lead of the helical slot path correspond thereto. The largest diameter at the proximal end of flank 42 is 32 mm and the smallest diameter of the flank at the opposite end is 13 mm. The core 40 has a diameter of 5 mm. The axial length of spindle 38 is about 52 mm. Recesses 48 are provided at the outside periphery of flank 42 and are spaced from one another by 90°. The trailing edge of each recess 48 is in the form of a cutting tooth.

The stem 12 has the following dimensions: overall length (without neck 17) 155 mm, width of end faces 16 proximally 10 mm and distally 8 mm, width of the broad side faces 14 proximally 50 mm and distally 8 mm.

The screw spindle 38 is inserted with its projecting distal core 40 into the bore 30 and then is rotated whereby the distal end of flank 42 finds the entry of slot 36 at the upside of bridge 28. From this moment the spindle 38 is guided positively to move on the predetermined helical path. After a complete revolution the distal flank end leaves bridge 28 and upon further screwing in the screw spindle 38 the distal end thereof passes through the window 18, the web 22 and window 20 until the projecting core end is received in a tap hole 44 of stem 12. During this screw-in motion of spindle 38 the peripheral self-cutting edge of flank 42 increasingly cuts into the cancellous bone structure adjacent to both broad side faces 14 of stem 12. During the last revolution or revolutions the peripheral edge of flank 42 additionally engages with the grooves 46 provided in legs 24, 26, whereby this broad-flanged flank 42 and the small-sized core 40 of spindle 38 is stabilized in addition.

The bridge 28 and the stiffening web 22 are designed to provide that the upside and bottom side surfaces thereof respectively tightly adjoins the neighbouring portions of flank 42 in order to weaken bridge 28 and web 22 as small as possible.

When spindle 38 has been completely screwed-in, flank 42 fills up the slots 36 in bridge 28 and web 22 and a plurality of segment-shaped flank portions project laterally from both side faces 14 of stem 12. These flank portions form broad-flanged lateral supporting ribs and the radial dimensions thereof are sufficient not only to cut into the cancellous bone structure but also into the surrounding cortex. In this embodiment the radial dimension of the proximal supporting rib amounts to 11 mm.

A hole 50 is provided in bridge 28 and an anti-rotation securing pin 52 is screwed in to the hole 50, which is so arranged that pin 52 passes one of the recesses 48 of flank 42.

The windows 18, 20 in principle can be omitted however, they are favorable for an ingrowth of cancellous bone structure into the cavities formed between the core 40 of spindle 38 and the stem legs 24, 26 respectively. In the embodiment shown in the drawings the windows 18,20 are of an approximate trapezium shape, whereby the angle between both diverging sides is substantially equal to the cone angle of the flank 42 of spindle 38. The segment-shaped or ring-shaped grooves 46 have the same depth.

I claim:

1. A cementless endoprosthesis primarily for hip joints comprising:
    a longitudinal stem to be non-rotably inserted into a medullary canal, the stem at a proximal end thereof having a conical neck integral therewith, said neck having a central axis angularly arranged with respect to a central longitudinal axis of the stem, said stem having a pair of broad side faces and a pair of small end faces, the stem including means for guiding and supporting a screw spindle; and
    said screw spindle having a broad flange helical flank to engage cancellous bone of the canal, whereby upon being screwed into the stem in a substantially longitudinal direction, the flange helical flank is extended beyond both side faces of the stem to form a plurality of lateral extending support ribs cutting into cancellous bone of the canal.

2. An endoprosthesis as claimed in claim 1, wherein the stem is provided with at least one window forming a passage between both side faces, the screw spindle passing through said window, and hollow spaces are provided between the core of the screw spindle and each one of a pair of legs formed between the window and said pair of small end faces of the stem respectively.

3. An endoprosthesis as claimed in claim 2, wherein at least one of the legs is provided with grooves at the inner surface facing the window, said grooves arranged on a helical path coinciding with the helical flank of the screw spindle and wherein the screw spindle is in threaded engagement with said grooves when the screw spindle is completely screwed in.

4. An endoprosthesis as claimed in claim 1, wherein the axis of the screw spindle is inclined in the direction of the neck with respect to the longitudinal axis of the stem by an angle in the range of 2° to 10°.

5. An endoprosthesis as claimed in claim 1, wherein the stem is provided with a bore of circular cross-section, the bore beginning at the proximal upper surface of the stem and extending substantially in longitudinal direction thereof and wherein a slot is provided in the stem, the slot also beginning at the upper stem surface and running along a helical path in distal direction, the axis of the helical path coinciding with the axis of the bore, and the slot communicates with the bore in radially inward direction and is open at both broad side faces of the stem, and wherein the diameter of the bore is substantially equal with the core diameter of the screw spindle, the lead of the slot is equal with that of the helical flank of the screw spindle, the height of the slot is substantially equal with the thickness of said flank and the outside diameters of the slot and of the flank of the screw spindle correspond to one another in each radial plane within the cross-sectional area of the stem, and wherein the core and the flank of the screw spindle snuggly fit in the bore and the slot of the stem respectively and a plurality of lateral ribs one above another projecting outwards from both broad side faces of the stem and having a circular segment shape respectively are formed by the flank of the screw spindle.

6. An endoprosthesis as claimed in claim 1, wherein the outside contour of the screw spindle is substantially in the form of a truncated cone.

7. An endoprosthesis as claimed in claim 1, wherein the axis of the screw spindle intersects the longitudinal axis of the stem at a point which is proximally offset from a point of intersection between that longitudinal axis of the stem and the elongated axis of the neck.

8. An endoprosthesis as claimed in claim 2, wherein a bridge arranged above the window forms the proximal end of the stem, the bridge connecting both said legs with one another comprises a bore coaxially arranged with respect to the screw spindle axis, the core of the screw spindle is mounted for rotation in said bore, a slot is provided in said bridge, the slot arranged on a helical path communicating with said bore and having a lead and a height equal with the lead and the height of the flank of the screw spindle, respectively, wherein the slot opens at the upper and lower surfaces of the bridge, the screw spindle beeing screwed in through said bridge extends completely through said at least one window substantially in the longitudinal direction of the stem.

9. An endoprosthesis as claimed in claim 8, wherein the slot is open at both broad side faces of the stem.

10. An endoprosthesis as claimed in claim 1, wherein the screw spindle has a cylindrical core which projects axially from the flank thereof at the distal end and is fitted into a tap hole provided in the stem.

11. An endoprosthesis as claimed in claim 1, wherein the screw spindle has a cylindrical core of circular cross-section and the diameter of the core amounts to 30 percent at most of the greatest diameter of the helical flank of the screw spindle.

12. An endoprosthesis as claimed in claim 1, wherein a bore is provided in the proximal upside surface of the stem and extends substantially parallel with the longitudinal axis of the stem and a pin is inserted into the bore, the pin engaging with a recess of the flank of the screw spindle to prevent rotation thereof.

* * * * *